(12) United States Patent
Lauks

(10) Patent No.: US 7,824,529 B2
(45) Date of Patent: *Nov. 2, 2010

(54) ELECTRODE MODULE

(75) Inventor: Imants R. Lauks, Ottawa (CA)

(73) Assignee: Epocal Inc., Ottawa, Ontario (CA)

( * ) Notice: Subject to any disclaimer, the term of this patent is extended or adjusted under 35 U.S.C. 154(b) by 1351 days.

This patent is subject to a terminal disclaimer.

(21) Appl. No.: 11/041,453

(22) Filed: Jan. 25, 2005

(65) Prior Publication Data

US 2005/0150761 A1 Jul. 14, 2005

Related U.S. Application Data

(63) Continuation-in-part of application No. 09/871,823, filed on Jun. 4, 2001, now Pat. No. 6,896,778.

(51) Int. Cl.
*G01N 27/403* (2006.01)

(52) U.S. Cl. .............. 204/400; 204/403.02; 204/403.06; 204/409

(58) Field of Classification Search ................ 204/400, 204/403.02, 403.05, 403.06, 406, 409
See application file for complete search history.

(56) References Cited

U.S. PATENT DOCUMENTS

| | | |
|---|---|---|
| 4,053,381 A | 10/1977 | Hamblen et al. |
| 4,062,750 A | 12/1977 | Butler |
| 4,123,701 A | 10/1978 | Josefsen et al. |
| 4,133,735 A | 1/1979 | Afromowitz et al. |
| 4,225,410 A | 9/1980 | Pace |
| 4,250,010 A | 2/1981 | Kondo et al. |
| 4,301,414 A | 11/1981 | Hill et al. |
| 4,449,011 A | 5/1984 | Kratochvil et al. |
| 4,549,951 A | 10/1985 | Knudson et al. |
| 4,551,209 A | 11/1985 | Lauks |

(Continued)

FOREIGN PATENT DOCUMENTS

EP 0 366 795 A1 * 1/1989

(Continued)

OTHER PUBLICATIONS

Baker, "Smart Cards from a Manufacturing P.O.V.", *Solid State Technology*, 1992, 35 (10), pp. 65-70.

(Continued)

*Primary Examiner*—Kaj K Olsen
(74) *Attorney, Agent, or Firm*—Borden Ladner Gervais LLP

(57) ABSTRACT

A chip-carrier module known from smart card technology is adapted as an electrode array for use in disposable sensing or separation devices containing electrodes. The electrodes are manufactured directly onto chip-carrier module. The preferred electrode module includes a chip-carrier module and at least one electrode formed thereon, the chip-carrier module being a laminate of a metal foil and an insulator foil, which metal foil is divided into at least two conductor regions, the insulator foil having a perforation over each conductor region, and the at least one electrode being formed by a membrane layer applied to the insulating foil to extend through one of the perforations for electrical contact with the conductor region associated therewith, the membrane layer imparting chemical sensitivity to the electrode. The result is an electrode module for use in disposable sensing or separation devices containing electrodes, whose unit cost of manufacture is low even at modest manufacturing volume.

12 Claims, 5 Drawing Sheets

U.S. PATENT DOCUMENTS

| | | | |
|---|---|---|---|
| 4,613,422 A | 9/1986 | Lauks | |
| 4,629,424 A | 12/1986 | Lauks et al. | |
| 4,739,380 A | 4/1988 | Lauks et al. | |
| 4,864,229 A | 9/1989 | Lauks et al. | |
| 4,874,500 A | 10/1989 | Madou et al. | |
| 4,908,112 A | 3/1990 | Pace | |
| 4,933,048 A | 6/1990 | Lauks | |
| 4,954,087 A | 9/1990 | Lauks et al. | |
| 5,008,616 A | 4/1991 | Lauks et al. | |
| 5,009,766 A | 4/1991 | Lauks | |
| 5,041,395 A | 8/1991 | Steffen | |
| 5,063,081 A | 11/1991 | Cozzette et al. | |
| 5,096,669 A | 3/1992 | Lauks et al. | |
| 5,096,699 A | 3/1992 | Gaffar et al. | |
| 5,112,455 A | 5/1992 | Cozzette et al. | |
| 5,124,661 A | 6/1992 | Zelin et al. | |
| 5,141,868 A | 8/1992 | Shanks et al. | |
| D332,833 S | 1/1993 | Lauks et al. | |
| 5,192,412 A | 3/1993 | Kambara et al. | |
| 5,200,051 A | 4/1993 | Cozzette et al. | |
| 5,212,050 A | 5/1993 | Mier et al. | |
| D337,164 S | 7/1993 | Lauks et al. | |
| 5,391,250 A | 2/1995 | Cheney, II et al. | |
| 5,416,026 A | 5/1995 | Davis | |
| 5,447,440 A | 9/1995 | Davis et al. | |
| 5,466,575 A | 11/1995 | Cozzette et al. | |
| 5,514,253 A | 5/1996 | Davis et al. | |
| 5,554,339 A | 9/1996 | Cozzette et al. | |
| 5,593,638 A | 1/1997 | Davis | |
| 5,605,664 A | 2/1997 | Lauks et al. | |
| 5,609,824 A | 3/1997 | Lauks et al. | |
| 5,614,416 A | 3/1997 | Lauks et al. | |
| 5,628,961 A | 5/1997 | Davis et al. | |
| 5,638,828 A | 6/1997 | Lauks et al. | |
| 5,653,243 A | 8/1997 | Lauks et al. | |
| 5,666,967 A | 9/1997 | Lauks et al. | |
| 5,727,548 A | 3/1998 | Hill et al. | |
| 5,759,364 A | 6/1998 | Charlton et al. | |
| 5,779,650 A | 7/1998 | Lauks et al. | |
| 5,789,253 A | 8/1998 | Lauks et al. | |
| 5,821,399 A | 10/1998 | Zelin | |
| 5,824,033 A | 10/1998 | Ferrari | |
| 5,837,446 A | 11/1998 | Cozzette et al. | |
| 5,837,454 A | 11/1998 | Cozzette et al. | |
| 5,916,425 A | 6/1999 | Leader et al. | |
| 6,004,441 A * | 12/1999 | Fujiwara et al. | 204/403.14 |
| 6,004,442 A | 12/1999 | Choulga et al. | |
| 6,010,463 A | 1/2000 | Lauks et al. | |
| 6,030,827 A | 2/2000 | Davis et al. | |
| 6,306,594 B1 | 10/2001 | Cozzette et al. | |
| 6,379,883 B2 | 4/2002 | Davis et al. | |
| 6,438,498 B1 | 8/2002 | Opalsky et al. | |
| 6,750,053 B1 | 6/2004 | Opalsky et al. | |
| 7,074,610 B2 | 7/2006 | Cozzette et al. | |
| 2002/0177958 A1 | 11/2002 | Opalsky et al. | |
| 2003/0170881 A1 | 9/2003 | Davis et al. | |
| 2004/0018577 A1 | 1/2004 | Campbell et al. | |
| 2004/0175296 A1 | 9/2004 | Opalsky et al. | |
| 2005/0054078 A1 | 3/2005 | Miller et al. | |
| 2006/0046275 A1 | 3/2006 | Collier et al. | |
| 2006/0160164 A1 | 7/2006 | Miller et al. | |
| 2007/0015977 A1 | 1/2007 | McCann et al. | |

FOREIGN PATENT DOCUMENTS

| | | |
|---|---|---|
| EP | 0967480 | 12/1999 |
| EP | 1174711 | 1/2002 |
| JP | 6-56766 | 2/1991 |
| JP | 8-233778 | 9/1996 |
| WO | WO 98/09161 | 3/1998 |
| WO | WO 00/03222 A2 * | 1/2000 |
| WO | 0136958 A1 | 5/2001 |

OTHER PUBLICATIONS

Rankl et al., "Physical and Electrical Properties", *Smart Card Handbook*, Chapter 3, 1997, pp. 17-40.

Rankl et all, "Smart Card Manufacturing", *Smart Card Handbook*, Chapter 10, 1997, pp. 293-306.

Borchard, M. et al., "Disposable ion-selective electrodes", *Sensors and Actuators B. Elsevier Sequoia S.A.*, Lusanne, CH, vol. 25, No. 1-3, Apr. 1995, pp. 721-723, XP004309321.

Examination Report for European Patent Application No. 02740160.3, dated Aug. 21, 2008.

* cited by examiner

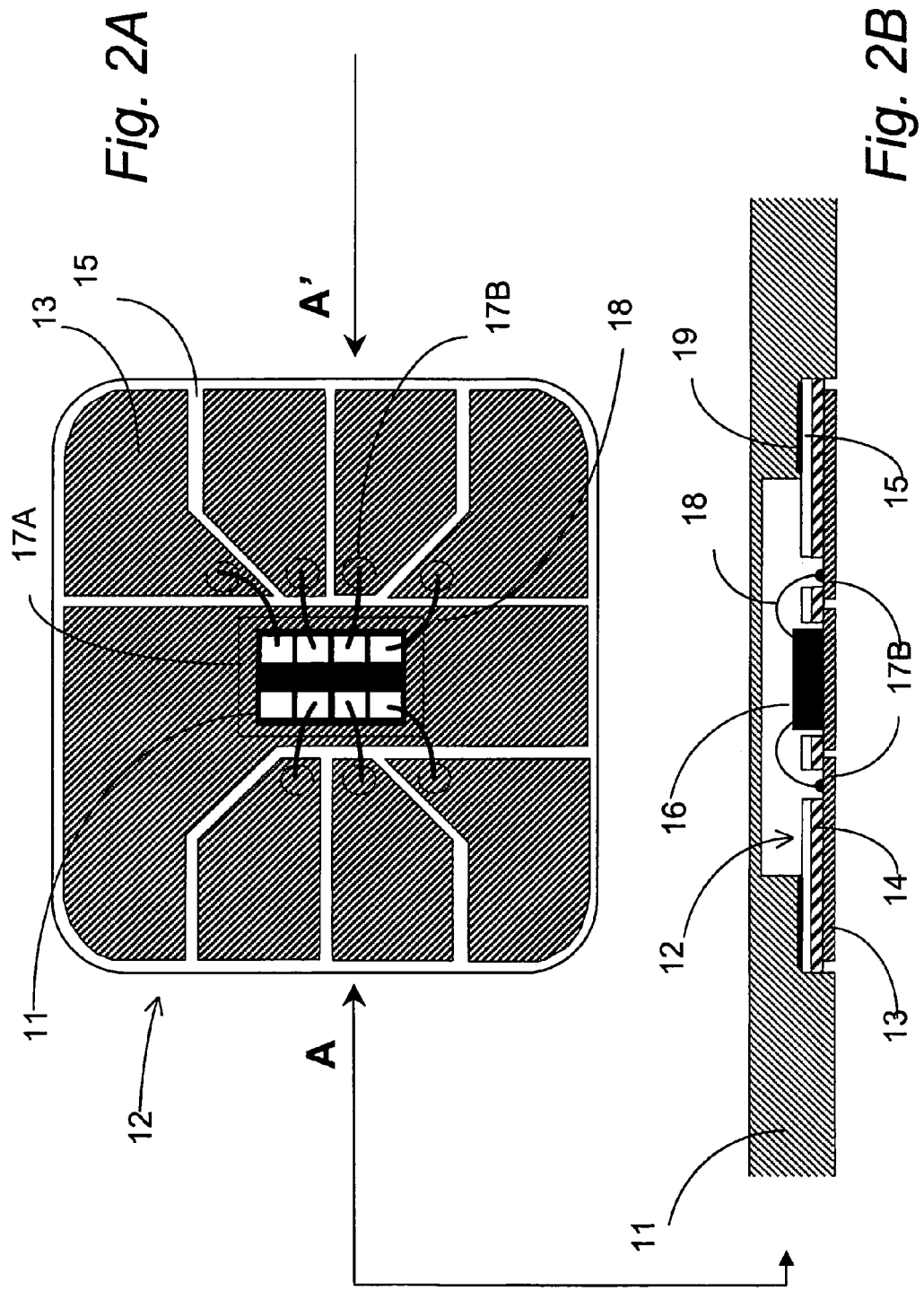

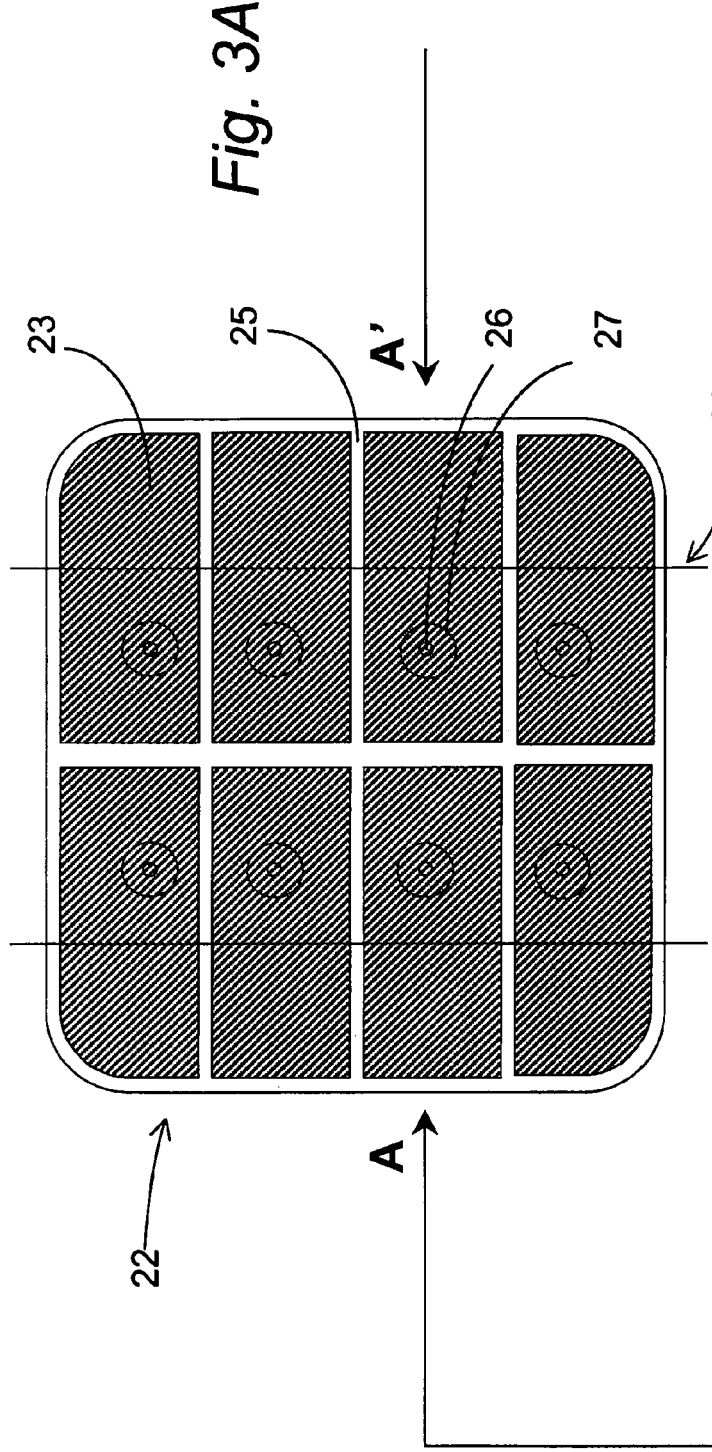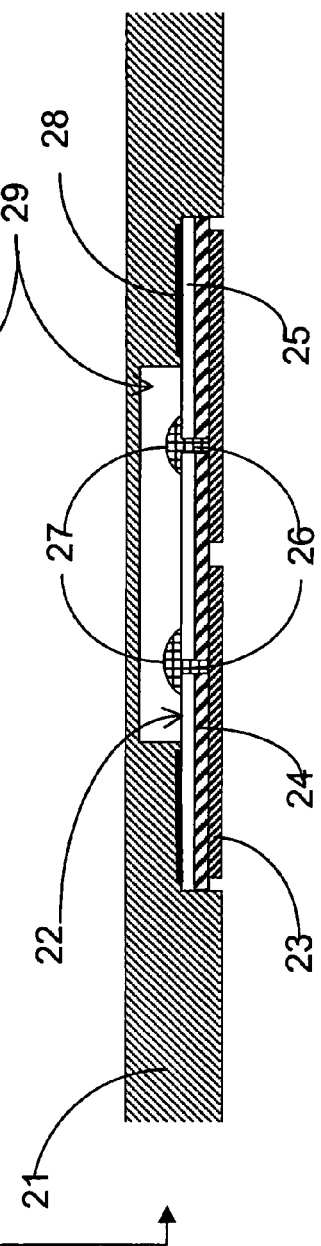

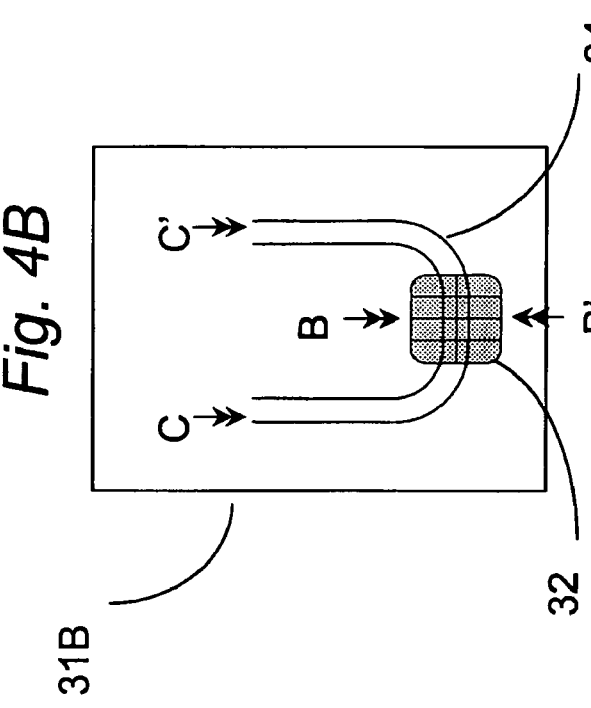
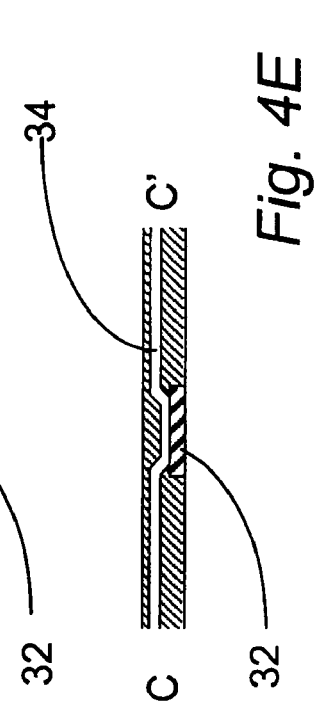
Fig. 4A
Fig. 4B
Fig. 4C
Fig. 4D
Fig. 4E

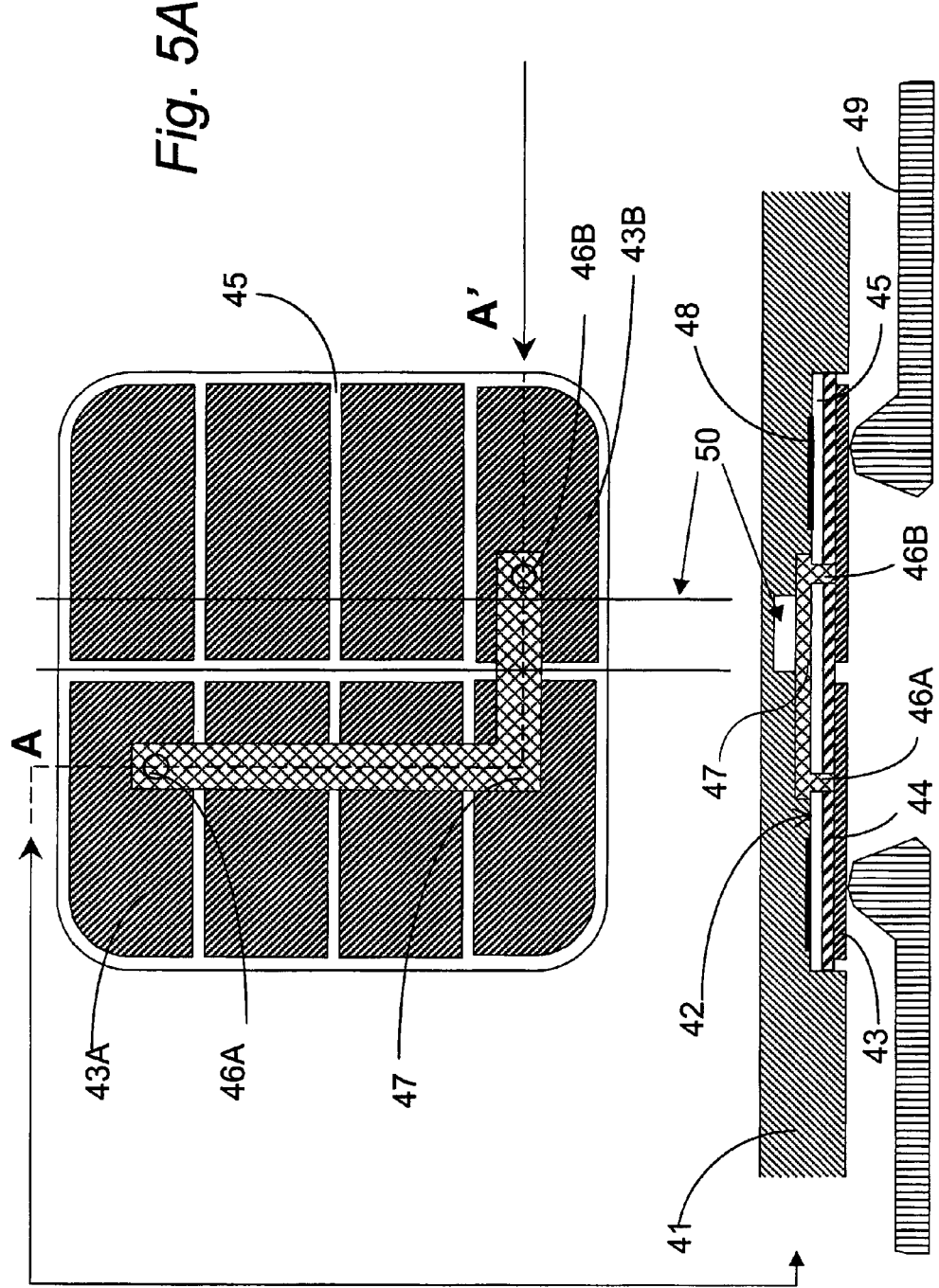

ELECTRODE MODULE

REFERENCE TO RELATED APPLICATIONS

The present application is a continuation-in-part of application Ser. No. 09/871,823 filed Jun. 4, 2001, entitled Electrode Module, now U.S. Pat. No. 6,896,778.

FIELD OF THE INVENTION

The invention is directed to diagnostic devices, particularly those designed for unit-use applications, incorporating planar chemical sensing electrodes and electrokinetic components and to methods of manufacture therefor.

BACKGROUND OF THE INVENTION

Numerous configurations of diagnostic devices incorporating planar electrodes have been described in the prior art. Planar electrodes contained within these prior art devices have been used as sensors (for example U.S. Pat. Nos. 4,053,381, 4,133,735, 4,225,410), in electrokinetic devices either as elements of electro-osmotic pumps or as electrodes for electrophoretic separation (for example U.S. Pat. No. 4,908,112), for electrical stimulation (U.S. Pat. No. 5,824,033), and the like. Common to all such prior-art devices is a planar electrical conductor with one location at which a contact is made to an external circuit or a measuring device, and a second location, the electrode, at which contact is made to an electrolyte. Often the electrode consists of one or more additional layers between the conductor and the electrolyte.

A design objective common to all such devices is the r&quirement to electrically insulate the conductor including the contact made to an external circuit from the electrode region in proximity to the electrolyte. Two general configurations have addressed this in the prior art. 1) Devices with planar conductors on planar supporting substrates have been configured so that the electrodes are contacted on the same surface as the electrolyte contact. Devices of this art are typically elongated so that there is a spatial separation between electrical contacts and electrolyte and there is electrical isolation of the conductor and the region of contact to the external circuit by an insulating barrier interposed between these two locations on the same electrode surface. 2) Devices with planar electrodes on planar insulating support substrates configured so that contact to the external circuit is made on the opposite surface to that at which the electrolyte makes contact. The electrode often traverses the substrate so that it is interposed between the electrolyte on one surface and the conductor contacts on the other surface. Devices of this type also are often elongated to spatially separate the contacts from the electrolyte.

Prior art planar diagnostic devices containing electrodes with same-surface contact configuration have been manufactured by a variety of different technologies. U.S. Pat. Nos. 4,133,735, 4,591,793, 5,727,548 for example disclose devices with electrodes made by thick film fabrication processes (printed circuit board technology, screen-printing, dispensing and the like). U.S. Pat. Nos. 4,062,750 4,933,048 and 5,063,081 disclose chip-like devices containing electrodes made by thin film micro-fabrication processes on silicon substrates. U.S. Pat. Nos. 4,053,381 and 4,250,010 disclose planar devices fabricated on conductor slabs or foils.

Prior art planar diagnostic devices containing electrodes with opposite-surface contact designs have been manufactured by a variety of technologies. U.S. Pat. No. 4,549,951 for example discloses thick film devices. U.S. Pat. Nos. 4,225,410 and 4,874,500 for example disclose micro-fabricated thick film devices.

Numerous electrode configurations have been disclosed in which the electrode forms part of a probe to be immersed in, or otherwise directly contacting a fluid. For example the prior art features planar electrode devices on catheter probes (for example U.S. Pat. No. 4,449,011), flexible electrode structures for subcutaneous measurement (for example U.S. Pat. No. 5,391,250) or for electrical stimulation (U.S. Pat. No. 5,824,033), as well as planar electrodes in diagnostic strip configuration for application of blood drops (for example U.S. Pat. Nos. 4,591,793 and 5,727,548). Other electrode configurations have been disclosed in which the electrode is designed as an element within a fluidic housing, which housing incorporates channels to provide for a flow of electrolyte to the electrode as well as to perform other fluidic manipulations such as calibration and reagent additions (for example U.S. Pat. Nos. 4,123,701 4,301,414; 5,096,669; 5,141,868; 5,759,364 and 5,916,425).

Mostly, prior art electrodes are expensive to manufacture on a per unit basis because they are structurally complicated or made with expensive materials. Even structurally simple electrodes can be costly at low manufactured volume, if they require specialized tooling and equipment for their manufacture. Such devices can only become inexpensive on a per unit basis when the volume is sufficiently large so that the large fixed cost of tooling and specialized manufacturing equipment can be absorbed by the large volume being produced. The cost issue becomes critical when the electrode is a component of a single-use disposable device. The configuration of devices as unit-use disposables is particularly attractive to users of diagnostic or separation apparatus because the equipment can be very simple and the devices easy to use.

Disposable sensor electrodes of the prior art for home use glucose measurement can exhibit unit costs of only a small fraction of a dollar when manufactured at very large volumes, for example greater than 200 million devices per manufacturer per year. However, there are also numerous diagnostic applications of prior art devices where the unit volume is less than 10 million per year and the cost of manufacturing is on the order of dollars per device. These higher manufacturing costs mean that these prior art devices can be cost-prohibitive for commercially viable lower volume applications.

In the prior art electrokinetic devices, such as for example electrophoretic separation devices, there are no examples of articles of commerce known in which the separation cassette including the transport medium and electrodes is configured as a disposable. In the case of slab gel separation apparatus of the prior art, the slab of gel is used for a single separation then disposed of. The gel slab is cast into a cassette including reusable glass plates forming the upper and lower gel-slab surface and reusable spacers defining separation lanes. There are reusable electrodes for applying the electric field across the transport medium. Such a device is described in U.S. Pat. No. 5,192,412. Further known are micro-scale electrokinetic devices, so called lab-on-a-chip devices, consisting of empty capillary channels formed into planar substrates with integral electrodes, see for example U.S. Pat. No. 4,908,112. Such devices are complex to manufacture and also have not been configured as low cost disposables.

Thus there is a need for disposable sensor electrodes or electrokinetic transport electrodes that can be manufactured at very low cost even at modest manufactured volumes.

To reduce the cost of information storage devices for personal use, a technology unrelated to disposable diagnostic devices, integrated circuit chips are packed into the devices using smart-card technology or IC card technology. See for example the paper entitled "Smart Cards from a Manufacturing Point of View" by Baker in Solid State Technology 1992, 35(10), p 65-70. In the manufacturing of smart cards, integrated circuit chips are assembled, glued and wire-bonded onto chip-carrier modules (for example U.S. Pat. No. 5,041, 395). The chip-carrier module includes an insulating layer and a metal layer applied thereto forming a contacting region divided into a number of electrically separate contact areas. Multiple chip-carrier modules are manufactured in a tape format with the insulating layer being in the form of a tape and the metal layer being divided into a plurality of contacting regions along the tape. The purpose of the chip-carrier module is to provide a substrate on which to place and hermetically seal the tiny integrated circuit chip. The purpose is also to provide for contacting means so that the electrical signals can be directed from the chip to metal leads on the chip-carrier module via wire bonds. Because of the requirement for very low cost of the final smart-card device, the chip-carrier module was designed with low cost materials. Moreover, the tape format of the fabricated chip-carrier modules resulted in highly automated reel-to-reel chip assembly, wire-bond and hermetic sealing processes that are also low cost. Although it would be possible to replace the integrated circuit chips mounted on such chip-carrier modules with a conventional lab-on-a-chip device, the resulting manufacturing cost would still be prohibitive for use of this structure in disposable diagnostic devices.

SUMMARY OF THE INVENTION

It is an object of this invention is to provide an electrode module whose unit cost of manufacture is low even at modest manufacturing volume, for use in disposable sensing or separation devices containing electrodes.

It is a further object of the invention to provide disposable sensing and separation devices made of elements available at low cost.

It is another object of the invention to provide an electrode module structure for disposable sensing and separation devices, which is made with readily available low cost elements previously used only in the manufacture of unrelated smart cards.

To achieve a low cost packaging for micro-fabricated semiconductor chip-based sensor electrodes and separation devices, it would be possible to use the chip-carrier modules of smart cards as carriers for sensor or separation chips rather than for their intended use in electronic smart cards as carriers of integrated circuit chips. However, while such an adaptation of the smart card chip-carrier module would be feasible, it would still require the significant tooling and manufacturing cost associated with the gluing and wire bonding of the chip onto the chip-carrier module. It would also require the cost to manufacture the semiconductor chip-based devices.

It has now been surprisingly found by the present inventor that a different adaptation was greatly superior. For many diagnostic test types the chip-carrier module itself or a similar structure can be adapted for use as an electrode array.

Thus, it is yet another object of the invention to provide an electrode module for a disposable sensing and separation device, which module includes electrodes manufactured directly onto a chip-carrier module.

Throughout this specification, the terms carrier module and chip-carrier module are intended to include prior art chip-carrier modules typically for use in smart cards and all similar structures whether intended to function as a chip-carrier or not. The carrier module principally includes a laminate of an insulating layer and a metal layer, whereby the metal layer is divided into at least two metal conductor elements and the insulator layer preferably has at least one perforation per conductor element.

Devices with such electrode modules no longer require a micro-fabricated, chip-based electrode array, and their process of manufacture does not require the numerous steps of assembly, gluing and wire-bonding of a chip onto the chip-carrier module. The elimination of many materials and process steps thus makes electrode modules in accordance with the invention, and devices including them, far less expensive than a device with an electrode array contained on a diagnostic chip that is glued and wire-bonded to a chip-carrier module.

It is still another object of the invention to provide a sensor or sensor array by incorporating chemically or biologically active membranes in the electrode region of an electrode module.

It is another object of the invention to provide a device for electrokinetic fluid flow such as an electrophoretic separation device. Such a device can be realized by incorporating an electrokinetic conductor such as a hydrophilic matrix layer in the electrode region of an electrode module, the voltage across the electrokinetic conductor causing electrokinetic fluid flow being provided by a pair of electrodes of the electrode module.

It is yet a further object of the invention to provide electrode modules in a tape format and adapt the tape for use in an automated, reel-to-reel sensor or separation device fabrication process.

It is still a further object of this invention to provide an electrode module with a chip-carrier module having a conductor array geometry that is standardized to the geometry of smart cards such as a chip-carrier as described in the relevant industrial standards established by the standards organizations ISO and AFNOR, in particular ISO 7816-2. This enables the use of diagnostic devices according to this invention with standard, off-the-shelf smart-card contacting components with minimal modification. Details of the relevant dimensions are also contained in "Smart Card Handbook by W. Rankl and W. Effing, John Wiley & Sons, 1997."

Throughout this specification, a carrier module, for example a chip-carrier module, modified by direct application of electrodes thereonto is referred to as an electrode module.

In a preferred embodiment of the invention, the electrode module includes a chip-carrier module and at least one electrode formed thereon, the chip-carrier module being a laminate of a metal foil and an insulator foil, which metal foil is divided into at least two conductor regions, the insulator foil having a perforation over each conductor region, and the at least one electrode being formed by a membrane layer applied to the insulating foil to extend through one of the perforations for electrical contact with the conductor region associated therewith, the membrane layer imparting chemical sensitivity to the electrode.

Electrode modules of the current invention incorporate elements that are both very simple in construction and of a configuration which renders them suitable for low cost highly automated fabrication. The components of the devices in accordance with the invention are exceedingly inexpensive to manufacture. Some preferred elements of the device of the invention are already being manufactured at high volume for their prior art intended use in cost sensitive electronic smart-card applications. The large volume of units manufactured primarily for smart cards absorbs the significant tooling costs and specialized manufacturing equipment costs. Thus, those elements are available at low cost and applicable for use in lower-volume medical-diagnostic applications when modified for use in a device in accordance with the current invention.

It is a further object of the invention to provide an electrode module, alone or with additional sensor membranes or electrokinetic conductor layers, that can be used in conjunction with a housing element containing fluidics (conduits, openings and the like).

It is another object of this invention to provide a disposable diagnostic device including an electrode module according to the invention, standardized connection geometry and a structure for device identification, for example a magnetic strip. This enables the use of the medical diagnostic or separation devices according to this invention in connection with off-the-shelf combination smart card connector components/magnetic strip readers with minimal modification.

It is a further object of this invention to provide devices with good immunity to electrical noise. This object is met by providing suitably large electrode surface areas, and at the same time providing a device geometry that keeps the distance between a respective high impedance electrode element and pre-amplifiers of an external circuit as short as possible.

Diagnostic devices in accordance with this invention are also contemplated which include on a chip-carrier module both electrode elements (for sensing or separation) as well as a chip (for sensors, separation devices or integrated circuits). It is thus a further object of this invention to provide such a device in which the carrier module serves both as an electrode array and a chip carrier in a single diagnostic device.

The diagnostic device according to a preferred embodiment of this invention consists of a body element, typically a plastic component in the general shape of and with the dimensions of a credit card. The body element functions as housing and contains fluidics (openings and conduits to allow the introduction and movement of analyte, reagents or calibrants). The body element also contains a cavity dimensioned for receiving an electrode module in accordance with the invention. The electrode module, when embedded in the housing, preferably has its outer face substantially flush with the face of the card-like body element. The configuration of the electrode module, and its placement in the body element generally conforms to the card configuration ID-1 or the smaller ID-00 or ID-000 configuration (for those diagnostic devices requiring less fluidics) specified by ISO 7810, 7816-1 and 7816-2 and also described in "Smart Card Handbook", supra.

It will be appreciated that it is advantageous to keep the length and width of the card-like body element in conformance with standard specifications so as to enable use of standardized connector technology as well as to enable the use of standardized manufacturing equipment for the card assembly. However, the thickness of the body element can be different from the conventional 0.76 mm flat card specification in order to accommodate fluidic elements within the card-like body.

BRIEF DESCRIPTION OF THE DRAWINGS

The preferred embodiment of the invention will now be further described by way of example only and with reference to the following drawings, wherein

FIG. 2A is a plan view of a prior art smart card;

FIG. 2B is a cross-section through the prior art smart card of FIG. 2A taken along line A-A;

FIG. 3A is a top plan view of a multi-electrode module in accordance with the present invention;

FIG. 3B is a cross-section through the module of FIG. 3A when installed in a housing;

FIGS. 4A-4E schematically illustrate the relationship of the electrode module to fluidic elements in the housing of a device in accordance with the invention;

FIG. 5A is a schematic top view of an electrode module in accordance with the invention including a channel for electrokinetic flow and electrodes; and FIG. 5B illustrates the module of FIG. 5A in cross-section taken along line A-A' and installed in a housing.

DETAILED DESCRIPTION OF THE PREFERRED EMBODIMENT

Figure 1:
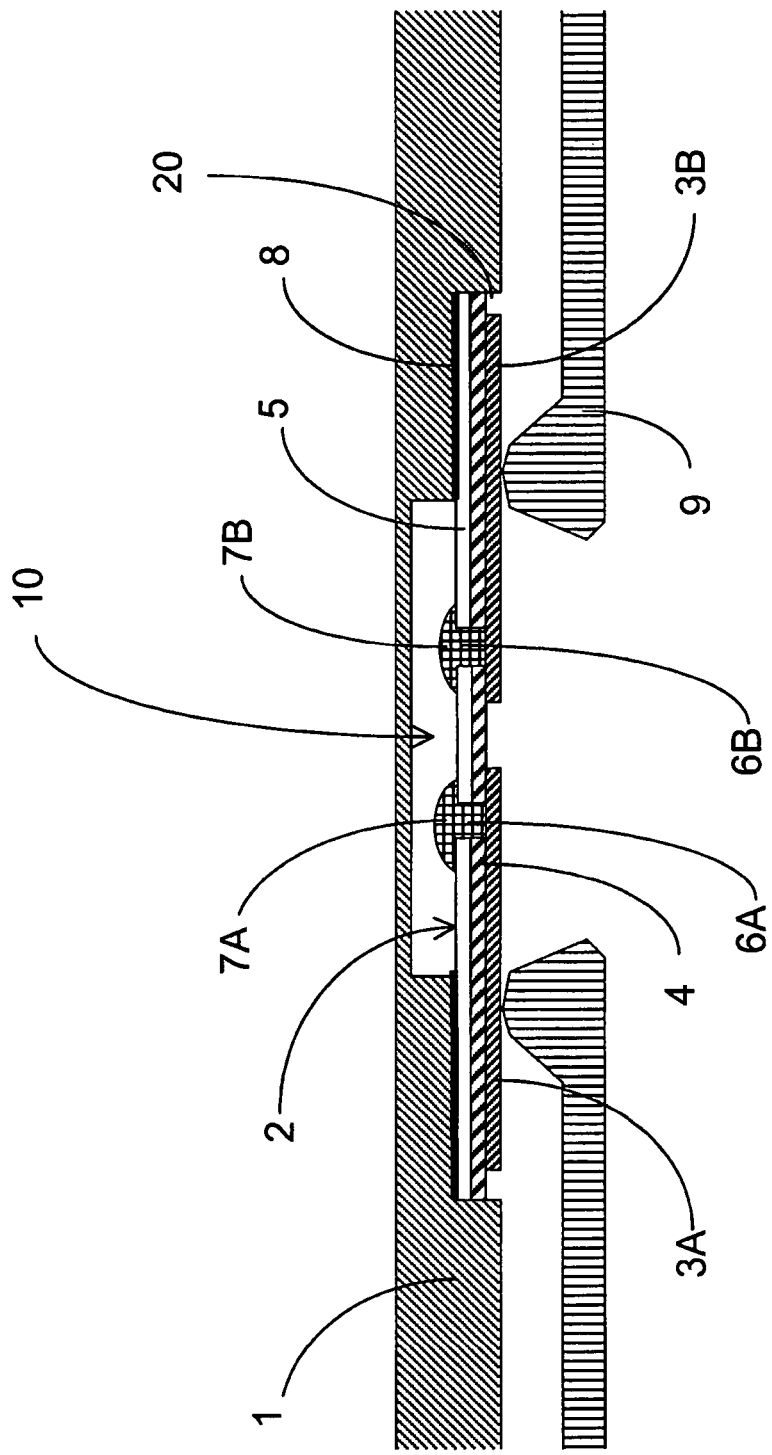
FIG. 1 is a horizontal cross section through the preferred embodiment of a diagnostic device according to this invention.

The present invention relates to planar electrode modules with electrodes for performing chemical analyses and to diagnostic devices including them.

FIG. 1 shows in detail a preferred embodiment of a diagnostic device in accordance with the invention for performing a chemical analysis of a species. The device includes an electrode module 2 in a housing 1. The housing is a thin plastic card similar in shape and size to a smart card or a credit card. The housing contains a module cavity 20 appropriately sized to accept the electrode module. The housing preferably contains additional other cavities, channels, and openings suitable for introduction of a fluid sample and its further manipulation within the housing for the purpose of performing an intended diagnostic procedure within the device. These other cavities and channels are collectively known in the art as fluidics and are discussed in more detail below with reference to FIG. 4.

The electrode module 2 of the device shown in FIG. 1 includes a carrier module 2A and a pair of electrodes 7A, 7B. Although it is preferred to use a conventional chip-carrier module as the carrier module 2A for ease of availability and low unit cost, it is easily understood that other carrier modules consisting of a laminate of an insulating layer with a metal layer can be used. The chip carrier used in the embodiment of FIG. 1 is die-cut from a substantially planar sheet consisting of a laminated bi-layer of a metal layer 3 and a thin film insulator layer 5 with an optional adhesive layer 4 therebetween. The electrodes will be described in more detail below. The chip carrier 2A is a planar sheet with an inner face, the insulator layer 5, an outer face, the metal layer 4 and a perimeter. The electrode module 2 is embedded in a module cavity 20 in the fluidic housing 1 with its inner face oriented into the cavity. The module 2 is sealed in relation to the housing using a seal layer 8. Electrode openings 6A and 6B through the insulator 5 define the location of the two electrodes of the module. The metal layer 3 is spatially divided into two separate metal conductor elements 3A, 3B. Each metal conductor element extends over a region beyond the electrode openings 6A, 6B to a location at which contact can be made to an external circuit (not illustrated) by engaging contacting elements 9 with the outer surface of the electrode module 2. These contacting elements 9 are contained within a connector device (not illustrated). Appropriate connector devices for smart cards, so-called smart card connectors as part of smart card readers are well known and need not be discussed in detail herein. At the electrode openings 6A and 6B, the insulator layer 5 is respectively coated with one or more thin film over-layers or membrane layers 7A, 7B of electrochemical material which extend through the openings and into contact with that metal conductor element 3A, 3B respectively surrounding the opening. The metal conductor element and the respectively contacting membrane layer 7 together form an electrode. Electrochemical materials which can be used for these membrane layers are well known in the art and include immobilized electrolytes and ion selective membranes in ion sensors, bio-layers containing enzymes in enzyme electrodes and other related bio-sensors, immobilized electrolytes and gas permeable layers in gas sensing electrodes. The membrane layers 7 impart chemical sensitivity to the electrodes, which are preferably used for sensing. In such an electrochemical cell with a pair of electrodes, one electrode will usually generate an electrical signal in proportion to a species concentration. That electrode is called the sensor or working electrode. The other electrode is called the reference electrode.

In use, a sample of fluid is collected into the housing of the diagnostic device in accordance with the invention. The device is inserted into a connector device (not shown) that includes an array of contacting elements or pins 9. The connector device is similar to that used for smart card connection within a smart card reader. The diagnostic device of the invention, with its precisely located metal conductor elements 3 of the electrode module 2, is engaged to the connector device so that the metal conductor elements 3A and 3B of the metal layer 3 (see FIG. 1), which metal layer 3 is the lowermost layer of the electrode module 2 and forms the lowermost surface of the module, respectively come into electrical contact with a contacting element 9 of the connector device. Those skilled in the art will appreciate that the order in which the operations of sample collection and insertion into the connector device are performed might depend on the type of chemical analysis being performed, and either order is within the scope of the invention. In either case, at a point in the use of the invented device the sample fluid is positioned in the module cavity 20 over the electrodes of the electrode module which module cavity is preferably part of a fluidic conduit 10. An electrical signal is developed at the electrodes when the sample fluid comes into contact with the sensor membranes 7 over the electrode openings 6. The electrical signal from the electrode pair is taken through the contacting elements 9 of the connector device to an external circuit (not shown) where it is related to the concentration of a species being analyzed within the sample. Those skilled in the art will appreciate, for example, that electrical current, voltage or conductance could be measured at the electrodes and related to a chemical concentration in the sample fluid. Other operations may also be performed in the chemical analysis procedure using a diagnostic device in accordance with the invention. Operations such as calibration and addition of reagent are often performed within fluidic housings of analytical devices. Such other fluidic operations are clearly contemplated in the design of the device according to this invention.

The housing 1, with its cavity 20 for the electrode module 2 and its fluidic structures (see FIGS. 4B-4E), can be manufactured from PVC or ABS as is known in the art of smart cards, although other materials such as polycarbonate also are suitable. The cavities and fluidic structures can be fabricated by molding the housing (preferred in the case of ABS) or by mechanical or laser machining or die-cutting of blank card stock (die-cutting and mechanical machining being preferred in the case of PVC). A combination of molding and machining also can be used. Those machining processes are known to the person skilled in the art and need not be discussed further herein.

As mentioned, the carrier module 2A of the electrode module 2 is an element made by lamination of a metal foil 3 with a perforated insulating foil 5. Copper foil is the preferred material for the metal foil. Individual metal conductor elements are preferably rendered in the copper foil by a photo etch process, although die-cutting is also known in the art. It is preferred that the copper be additionally coated with plated layers of first nickel then gold. Gold is a stable material and preferred for the electrodes of the diagnostic device of the present invention. The insulator layer 5 is a thin plastic sheet made from a material such as polyimide, mylar, nylon or epoxy. For low cost and thermal stability in downstream manufacturing processes, epoxy is the preferred choice of insulator material. The electrode openings 6A, 6B are fabricated by die-cutting of the insulator foil as the preferred low cost method, although those skilled in the art appreciate that other perforation technologies are possible. The lamination process is performed by pressing together the metal foil and the insulator. A seal is thus formed by the adhesive 4 interposed between the two layers. Epoxy glue formulations are preferred. The lamination process is generally performed on continuous sheets of the foils which are unwound from reels. The fabricated laminated sheet is in the form of a strip and is again wound up onto reels. The conventional 35 mm tape format is preferred for low cost manufacturing and handling. The laminated strip contains many carrier modules. For automation of the electrode forming process, the membrane layers 7A, 7B are preferably deposited onto the insulator layer 5 around the openings 6A, 6B while the chip carriers are still on the strip, as described later in more detail. Individual electrode modules are separated from the strip preferably by a die-cutting process before they are embedded and sealed into the housing 1. The seal can be a sealing layer 8 of an adhesive material which is dispensed onto the sealing surface of the housing or onto the insulator layer 5 of the electrode module 2. In the alternative, the sealing layer is in the form of an adhesive tape applied to the sealing surface of the housing or the module. It is also acceptable to form a seal by heat welding of the module surface to the housing surface, for example by heat deforming that part of the housing 2 surrounding the module cavity 20 to mold it around outside edges of the module in the module cavity. The seal can also form when the module is insert-molded during the card molding process if that is the technique used to produce the card. In all cases it is the intention to seal the module in the module cavity. Although the accompanying Figures show the seal on the inner module surface, equivalent sealing layers 8 can be located at the module edge, about its perimeter, or even on the outer surface at the perimeter.

Preferably, the seal not only mechanically retains the electrode module 2 in the housing 1, but also ensures that the fluids within the housing remain on the inner surface of the module where the electrodes are located and that fluids do not leak to the outer surface of the module where the electrical contacts are located.

FIGS. 2A, 2B and 3A, 3B are useful to compare a chip-on-chip-carrier module of the prior art with and contrast it from the electrode module of the current invention. FIGS. 2A and 2B show a multi-lead chip-carrier module in its prior art intended use in a smart card module with an integrated circuit chip wire-bonded thereto. FIGS. 3A and 3B respectively show a multi-electrode embodiment of an electrode module and a diagnostic device according to this invention. FIG. 3B depicts an electrode module made of a chip-carrier and electrodes directly applied thereto, which module is mounted in a fluidic housing. Preferably, both the dimensions of the electrode module of the current invention shown in FIG. 3B and its placement within the housing are similar to the dimensions and placement of the chip on chip-carrier module combination of the prior art as shown in FIG. 2B, (to within the tolerances specified in ISO 7816) so that off-the-shelf smart card connectors can be used for the diagnostic application of the current invention with minimal modification.

FIGS. 2B and 2A respectively show a detailed cross-section and plan view of a chip-carrier module of a prior art smart card. These diagrams show a housing 11 for the chip-carrier module 12. The chip-carrier module 12 consists of a lamination of a first copper layer 13 with an insulator layer 15 sandwiching a glue layer 14. The copper layer is spatially divided into metal conductor regions. There are 8 regions shown in standard smart card geometry in FIG. 2A. The insulator layer 15 is perforated by a die-cutting process to provide apertures 17. An integrated circuit chip 16 is located on the chip-carrier module 12 over a large centrally located perforated aperture 17A. The chip is attached to the metal of the module with glue. Wire-bonds 18 electrically connect the bonding pads of the integrated circuit chip with the metal conductor elements of the chip-carrier module through other apertures 17B of the insulator 15. Chips are mounted and wire-bonded onto the chip-carrier modules while the modules are still contained on a strip previously stored on a reel. A hermetically sealing glue layer (not shown) is then applied over the chip and wire-bonds. Individual modules are separated from the strip and embedded into smart card housings, then sealed using sealing means 19. The geometric arrangement of the metal conductor elements 13 and the placement of the chip-carrier module 12 within the housing are specified by ISO standard 7816.

A preferred multi-electrode sensor embodiment of the current invention is shown in FIGS. 3A and 3B. The carrier module 22A of the electrode module 22 of this embodiment of the invention has a similar configuration of metal conductor elements as the chip-carrier module in the prior art smart card of FIGS. 2A, 2B. Thus, key dimensions such as the size and pitch of the contacting regions of the metal conductor elements and the position of the module with respect to the edges of the housing 21 are in accordance with specifications established by ISO standard 7816 (or the similar French AFNOR specifications). These specifications are described in more detail in the relevant published standards or for example in "Smart Card Handbook", supra. Using the standard dimensional specifications established for smart cards also for the electrode module of this invention enables the use of the device or the invention with minimally modified smart card connector devices that are off-the-shelf articles of commerce.

In the preferred multi-electrode sensor embodiment shown in FIGS. 3A, 3B the electrode module 22 located in the module cavity 30 contains an array of perforations through the insulator 25 which define electrode openings 26. Electrode membrane layers 27 are located over the electrode openings 26 so that they penetrate therethrough and contact metal conductor elements 23A, 23B located below the respective opening. The electrode array is located within a fluidic channel 29 of the housing 21. For illustration, the electrode array is shown with two rows of 4 electrodes each, which electrodes are of equal dimensions. The perforated electrode openings 26 of the electrode module 22 are typically smaller than the apertures of the chip-carrier module of FIG. 2. Those skilled in the art will recognize that there are many configurations of electrode position and geometry consistent with the specifications set out in this invention. Those skilled in the art will further recognize that there are still many electrode geometries possible with ISO 7816 metal conductor element specifications of the preferred embodiment of this invention. Thus for example, the electrode openings 26 may be a different size and shape for each electrode. The position of electrodes on the module is only restricted by their requirement to electrochemically contact the sample fluid within the channel, the ability to form the metal conductor elements connecting the electrodes 23 to contacting means and the ability to form a seal between the module and the housing. Configurations of other standardized modules such as those with six contacts also are within the scope of this invention.

FIGS. 4A-4E show schematics of the relationship of the electrode module to fluidic elements within the housing. The electrode module depicted in FIGS. 4A-4E is the 8-electrode embodiment described in FIG. 3, although the relationships of module to fluidic housing described here pertain to any of the module designs according to the specifications of this invention. Two main configurations of the module within the housing are depicted in the plan view schematics of FIGS. 4A and 4B. FIG. 4A shows a plan view of module 32 in housing 31A with an opening 33 in the housing directly above the module. Such a configuration is appropriate for a device in which sample is introduced directly onto the electrodes of the module. The cross-section between locations A and A' of the housing of FIG. 4A is shown in FIG. 4C. This Figure shows a lip around the opening to achieve sample retention to the electrode surface of the module 32.

FIG. 4B illustrates a plan view of a module 32 located in a conduit 34 within a fluidic housing 31B. The conduit 34 extends from locations C and C' within the housing, at which locations the conduit is connected to other fluidic structures not shown in the diagram. These other fluidic structures may be an opening for sample introduction, a pump, a junction to other conduits, a waste chamber and the like. The cross-section between locations B and B' of FIG. 4B is shown in FIG. 4D. The cross-section between locations C and C' of FIG. 4B is shown in FIG. 4E.

FIGS. 5B and 5A respectively show a detailed cross-section and plan view of a preferred embodiment with the electrode module in the housing directed to performing an electrokinetic separation or transportation step within the diagnostic device of the invention. FIGS. 5A, 5B illustrate an electrode array and an electrokinetic conductor layer through which chemical species are transported by electrokinetic force (electrophoresis or electroosmosis). The lamination of metal layer 43 and insulator 45 in the electrode module 42 of FIGS. 5A, 5B is substantially the same as described in the previous embodiment. The dimensions and placement of the electrode module are shown to conform to ISO 7816 specifications as for the previous embodiment of the invention. An electrokinetic conductor layer 47 is located over the insulator 45. The electrokinetic conductor layer in this embodiment is a narrow track of a hydrophilic matrix solid that traverses the surface of the insulator and connects at least two electrode locations on the module. In FIG. 5B the electrokinetic conductor 47 is electrically connected to metal conductor elements 43A and 43B through holes 46A and 46B. The electrokinetic conductor intersects a fluidic conduit 50 of housing 41 at a location along its length between electrode openings 46A, 46B.

This invention contemplates the use of an electrokinetic conductor 47 formed from a hydrophilic matrix layer by microfabrication as described later and in detail in applicant's co-pending patent application Ser. No. 09/871,821. However, it will be appreciated that the electrode module of this invention could also be adapted for use with electrokinetic conductors of prior art devices. Thus, prior art gel-slab devices as well as prior art micro-channel electrokinetic devices can be adapted for use with the modules of the current invention to convert those prior devices into ones with low-cost integral electrodes. In the case of the gel-slab device, the electrokinetic conductor is a gel lane, or an array of gel lanes, cast between two planar surfaces, as described in U.S. Pat. No. 5,192,412. For example, one surface is a corrugated surface with a set of parallel grooves each of which constitutes a mold-form for the gel that defines the shape of the lanes. The other surface, typically a flat insulating plate in the prior art devices, could be adapted to incorporate the electrode module of the current invention. In the case of the prior art microchannel device, an electrokinetic conductor element is formed by microfabricating a capillary channel, or array of such channels, into a planar insulating substrate. A flat plate placed over the substrate covers the open channels to complete the device. The electrokinetic conductor is an electrolyte fluid that is pumped into the empty channel at or before use of the device. In a modification to this device, the planar cover plate could be adapted to incorporate an electrode module of the current invention.

In the embodiment of FIGS. 5A and 5B, the electrokinetic conductor 47 consists of a hydrophilic matrix material composed of either monomeric or polymeric hydrophilic molecules that readily incorporate water. Examples are sugars, starches, alcohols, ethers, poly amino acids proteins and hydrophilic silanes and derivatized silanes. The hydrophilic solid matrix may consist of a hydrophilic polymer in an extended state such as in a gel. Absorption of water results in a gel-like polymer in which water is incorporated into polymer chain interstices. Examples of suitable materials are cross-linked polyvinyl alcohols, poly hydroxy methacrylates, polyacrylamides gelatins and silanes. The hydrophilic solid matrix may be formed from a latex. The hydrophilic matrix may also contain dry electrolyte salts (to achieve high internal osmolality for good water uptake), buffers (to regulate internal pH for control of swelling of the hydrophilic matrix and to regulate internal pH to control chemical species transport and reaction) and other reagents depending on the function of the device in which the conductor is used.

Photoformable formulations may also be used for the hydrophilic matrix. Additives to hydrophilic polymer materials that cause cross-linking upon exposure to radiation are well known. Such additives when formulated with the other components of the hydrophilic matrix render the cast polymer film photoformable.

The preferred process for photoforming is similar to the processing of a standard photoresist. A layer of the material is deposited onto a planar substrate, allowed to dry and then exposed to actinic radiation through a mask. The exposed film is then developed in bath of developing medium, or a developing medium spray or even a dry plasma process. For the wet development processes aqueous developing solutions are typically used. However, the preferred photoforming process utilizes completely dry plasma etching steps on hydrophilic materials designed to be ash free when plasma etched. This prevents leaching of salts or other chemicals from the matrix during the forming process. By way of example, a hydrophilic matrix material containing electrolyte salts and buffers is deposited on the planar substrate from an aqueous solution by spinning, spraying, printing or dipping. Spinning is preferred. A photoresist layer is coated thereon from a non-aqueous solvent. It is exposed and developed. The photoresist pattern is then transferred by etching into the underlying hydrophilic matrix material using a plasma process that leaves no ash in the etched areas. The plasma etch step concurrently removes the photoresist layer. For example, when the hydrophilic matrix contains only carbon, hydrogen, oxygen and nitrogen, an oxygen plasma will etch the material forming only volatile etch products and no ash. In this example the hydrophilic matrix should be formulated with non-metallic salts and buffers to be ash-free during oxygen plasma etching. Thus the compositions of the hydrophilic matrix and its electrolytes, buffers and reagents are preferably chosen to be suitable for ash-free plasma etch processing. Using the above described ash-free dry processing techniques one or more hydrophilic layers may be sequentially processed into formed structures without exposure to wet developers.

In a preferred microfabricated electrokinetic device the hydrophilic matrix electrokinetic conductor layer can be further overcoated by a microfabricated insulator (not shown in FIG. 5). The overcoating insulator would have an opening to enable contact with sample fluid in the conduit 50. Also preferred is that the insulator be permeable to water vapor so that the hydrophilic matrix of the electrokinetic conductor can be fabricated dry and wetted-up for use by incorporation of water through the insulator layer, as described in detail in applicant's co-pending application Ser. No.

The use of the preferred embodiment of the invention as shown in FIGS. 5A and 5B is discussed in the following. In use, a sample of fluid is collected and inserted into the housing of the diagnostic device of the invention to come into contact with the desired electrode on the insulator side of the electrode module 42. The device is then inserted into a connector device (not shown) that consists of an array of contacting elements or pins 49, preferably an off-the-shelf smart card reader device readily commercially available. The diagnostic device is engaged to the connector device so that the metal conductor elements 43 come into electrical contact with contacting elements 49 of the connector device. Those skilled in the art will appreciate that the order in which the operations of sample collection and insertion into the connector device are performed might depend on the type of chemical analysis or separation being performed, and either order is within the scope of the invention. In either case, at a point in the use of the diagnostic device the sample fluid is positioned over the region of intersection of electrokinetic conductor 47 and conduit 50.

Referring to FIGS. 4A and 4B, it is clearly intended that an alternative method of sample introduction may be envisaged, such as through an opening in the housing above the hydrophilic matrix conductor.

A voltage is then applied from an external circuit to metal conductor elements 43A and 43B through contacting pins 49. Those skilled in the art will appreciate that the application of a voltage across an aqueous electrolyte such as that contained within the hydrophilic matrix of the electrokinetic conductor 47 will cause movement of the electrolyte as a whole through the conductor by electro-endo-osmosis as well as movement of individual charged species within the electrolyte by electrophoresis. These processes can be used in the device to create a pump action and to effect transport of the sample fluid along the electrokinetic conductor, and also to effect a separation of species within the conductor because of their different electrophoretic mobilities.

Other operations may also be performed in the electrokinetic separation or transport procedure using the diagnostic device as described herein. Fluidic operations within the housing element 41 such as the addition of reagent to the sample or pumping of calibrant fluids are clearly contemplated in the design of the device according to this invention. The two principally different uses for the diagnostic device of this embodiment are the same as the principle uses of other prior art electrokinetic devices. The use of such devices in electrophoretic separations or as a component of an electro-osmotic pump are well known in the prior art of electrokinetic devices.

I claim:

1. An electrode module for use in a diagnostic device for performing chemical analysis of a species in a sample fluid and for electrical contact with a contacting element of a connector device, comprising
   a chip carrier module made of a planar laminated bi-layer of a metal layer and an insulator layer, the insulator layer having opposing first and second sides, the metal layer being located on the first side, forming a lowermost surface of the module and being divided into at least two conductor elements; and
   a membrane element located on the opposite, second side of the insulator layer, the membrane element being in electrical contact with one of the conductor elements through the insulator layer and together with the one conductor element forming an electrode, the membrane element being configured to contact the sample fluid; the membrane element being made of electrochemical material for imparting chemical sensitivity to the electrode and for developing an electrical signal at the electrode when the species comes into contact with the membrane element; the electrode module having an insulator side and a conductor element side and being configured to permit simultaneous electrical and sample fluid contact with the electrode through physical, electrical contact of the contacting element with the one conductor element on the lowermost surface of the electrode module and simultaneous sample fluid contact with the membrane element on the insulator side of the electrode module.

2. The electrode module as defined in claim 1, wherein the chip carrier module is a flexible chip carrier module, the metal layer is a metal foil and the insulator layer is an insulator foil and electrical contact by the contacting element is made opposite the membrane element.

3. The electrode module as defined in claim 2, wherein the metal foil is made of copper.

4. The electrode module as defined in claim 2, wherein the metal foil is made of copper coated with films of nickel and gold.

5. The electrode module as defined in claim 1, wherein the chip-carrier module is a chip-carrier conforming to ISO standard 7816.

6. The electrode module as defined in claim 1, wherein the metal layer is divided into at least two metal conductor elements and the electrode module includes at least one electrode for each metal conductor element.

7. The electrode module as defined in claim 1, wherein the insulator layer has a perforation over each metal conductor element and the membrane element extends through the perforation for electrical contact with the metal conductor element.

8. The electrode module as defined in claim 1, further comprising an electrokinetic conductor for electrokinetic transport of a solute species to the at least one electrode.

9. An electrode module for use in a diagnostic device for performing chemical analysis of a species in a sample fluid and for electrical contact with a contacting element of a smart card connector device, comprising
   a smart card chip carrier module made of a planar laminated bi-layer of a metal layer and an insulator layer, the insulator layer having opposing first and second sides, the metal layer being located on the first side, forming a lowermost surface of the module and being divided into at least two conductor elements; and
   a membrane element located on the opposite, second side of the insulating layer, the membrane element being in electrical contact with one of the conductor elements through the insulator layer; the membrane element and the one conductor element together forming an electrode and the membrane element being configured to contact the sample fluid and being made of electrochemical material for imparting chemical sensitivity to the electrode and for developing an electrical signal at the electrode when the species comes into contact with the membrane element, the electrode module having a membrane element side and a conductor element side and being configured to permit simultaneous electrical and sample fluid contact with the electrode through physical, electrical contact of the external contacting element with the one conductor element on the lowermost surface and simultaneous sample fluid contact with the membrane element on the insulator side of the electrode module.

10. The electrode module as defined in claim 9, wherein the electrode module includes at least one electrode for each metal conductor element.

11. The electrode module as defined in claim 10, wherein the insulator layer has a perforation over each metal conductor element and the membrane element extends through the perforation for electrical contact with the metal conductor element.

12. The electrode module as defined in claim 9, further comprising an electrokinetic conductor for electrokinetic transport of a solute species to the at least one electrode.

* * * * *